(12) United States Patent
D'Armiento et al.

(10) Patent No.: US 6,608,112 B1
(45) Date of Patent: Aug. 19, 2003

(54) USE OF METALLOPROTEINASE INHIBITORS IN THE TREATMENT AND PREVENTION OF PULMONARY EMPHYSEMA

(75) Inventors: Jeanine D'Armiento, New York, NY (US); Kiran Chada, North Brunswick, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/530,617

(22) PCT Filed: May 20, 1998

(86) PCT No.: PCT/US98/10265

§ 371 (c)(1),
(2), (4) Date: Oct. 10, 2000

(87) PCT Pub. No.: WO98/52575

PCT Pub. Date: Nov. 26, 1998

Related U.S. Application Data

(60) Provisional application No. 60/047,178, filed on May 20, 1997.

(51) Int. Cl.[7] .................. A61K 31/19; A61K 31/65; A61K 31/135
(52) U.S. Cl. .................. 514/575; 514/152; 514/656
(58) Field of Search .................. 514/575, 152, 514/656

(56) References Cited

U.S. PATENT DOCUMENTS 4,666,897 A * 5/1987 Golub et al. ................ 514/152
5,773,430 A * 6/1998 Simon et al. ................ 514/152
5,872,152 A * 2/1999 Brown et al. ................ 514/575

OTHER PUBLICATIONS

PCT International Search report of International Application No.PCT/US98/10265, dated Sep. 17, 1998 (Exhibit 2).
Christie, et al. Treatment of allergy and autoimmune disease with inhibitors of human soluble CD23 formation. Chemical Abstracts, vol. 124, No. 307588 R, Feb. 1, 1996, (Exhibit 3).
D'Armiento J, etal. Collagenase expression in the lungs of transgenic mice causes pulmonary emphysema. Cell Dec. 11, 1992;71(6):955–61 (Exhibit 4).
Grams F, et al. Structure determination and analysis of human neutrophil collagenase complexed with a hydroxamate inhibitor. Biochemistry Oct. 31, 1995; 34(43):14012–20 (Exhibit 5).
Janoff, A. Elastases and emphysema. Current assesment of the protease–antiprotease hypothesis. Am Rev Respir Dis Aug. 1985;132(2):417–33 (Exhibit 6).
Merck Index, 10th ed., Windholz et al, Ed., Merck, Dohm & Sharp, Rahway, NJ, 1985 #6065, 7204, 9021.*

* cited by examiner

Primary Examiner—Russell Travers
(74) Attorney, Agent, or Firm—John P. White; Cooper & Dunham LLP

(57) ABSTRACT

The invention provides a use of a metalloproteinase inhibitor for the preparation of a pharmaceutical composition for treating human pulmonary emphysema which comprises admixing the metalloproteinase inhibitor in an amount effective to treat human pulmonary emphysema and a pharmaceutically acceptable carrier. This invention also provides a pharmaceutical composition which comprises a metalloproteinase inhibitor in an amount effective to treat human pulmonary emphysema and a pharmaceutically acceptable carrier.

5 Claims, 9 Drawing Sheets

FIG. 4B

EM 21 EM 13 EM 18 EM 20 EM 22 EM 23 N2 N3 A1 A2 tRNA HL-60

Table I.

CLINICAL CHARACTERISTICS OF PATIENTS PRIOR TO SURGERY

| Label | Age | Sex | FVC (%) | FEV1 (%) | FEV1/FVC | DLCO % |
|---|---|---|---|---|---|---|
| EM1 | 70 | F | 1.89 (59) | 0.51 (22) | 27 | 37 |
| EM2 * | 35 | F | NM | NM | NM | NM |
| EM3 | 62 | F | 2.03 (67) | 0.71 (29) | 35 | 35 |
| EM4 | 45 | M | 3.25 (65) | 0.91 (24) | 28 | 41 |
| EM5 | 46 | M | 2.22 (49) | 0.61 (18) | 28 | 56 |
| EM6 | 59 | M | 2.75 (70) | 0.94 (33) | 34 | 37 |
| EM7 | 71 | F | 1.48 (48) | 0.34 (20) | 29 | 33 |
| EM8 | 63 | F | 1.66 (50) | 0.72 (26) | 43 | 27 |
| EM9 | 71 | F | 0.98 (42) | 0.35 (21) | 36 | 18 |
| EM10 | 62 | F | 1.50 (61) | 0.34 (19) | 23 | 13 |
| EM11 | 61 | M | 2.75 (68) | 0.94 (33) | 34 | 21 |
| EM12 | 70 | F | 1.61 (57) | 0.50 (25) | 31 | 7 |
| EM13 | 58 | M | 2.86 (72) | 0.82 (28) | 29 | 19 |
| EM14 | 69 | F | 2.00 (70) | 0.60 (29) | 30 | 34 |
| EM15 | 65 | F | 2.72 (75) | 0.51 (26) | 25 | 23 |
| EM16 | 66 | F | 0.70 (25) | 0.36 (16) | 52 | 11 |
| EM17 | 61 | F | 1.53 (61) | 0.64 (35) | 42 | 92 |
| EM18 * | 39 | F | NM | NM | NM | NM |
| EM19 | 68 | F | 1.31 (63) | 0.43 (29) | 33 | 37 |
| EM20 | 58 | F | 1.07 (44) | 0.74 (27) | 47 | 83 |
| EM21 | 54 | F | 1.32 (42) | 0.44 (19) | 33 | 15 |
| EM22 | 65 | F | 1.36 (48) | 0.48 (23) | 35 | 22 |
| EM23 | 60 | F | 1.35 (37) | 0.39 (14) | 29 | 30 |
| A1 | 39 | F | 2.15 (65) | 0.57 (20) | 26 | 22 |
| A2 | 42 | F | 1.13 (32) | 0.35 (13) | 31 | 28 |
| A3 | 54 | M | 3.0 (56) | 0.82 (21) | 27 | 23 |

*These two patients at the time of organ donation were found to have gross evidence of emphysema. Both were known long time smokers without a clinical diagnosis of emphysema. Due to the gross emphysema seen these lungs were not accepted for transplant and were included in the emphysema group.

EM-emphysema, A-alpha-1 antitrypsin
NM-not measured

FIG. 7

Table 2. Collagenase-1 Protein Detected by ELISA

| HUMAN SAMPLE | | PROTEIN (ng/ml) |
|---|---|---|
| EM 16 | emphysema | 21.5 |
| EM 19 | emphysema | ND |
| EM 20 | emphysema | 8.1 |
| EM 22 | emphysema | 6.7 |
| EM 23 | emphysema | 13.8 |
| A 2 | $\alpha$1 AT | ND |
| Nod | benign nodules | ND |
| N 3 | normal | ND |

FIG. 8

Table 3. Summary of Collagenase Expression

COLLAGENASE EXPRESSION

| Group | Yes | No | Total Patients |
|---|---|---|---|
| Emphysema | 22 | 1 | 23 |
| Normal | 0 | 8 | 8 |
| α -1 antitrypsin | 1 | 2 | 3 |

Collagenase Expression Rate:

22/23 in the emphysema group vs. 0/8 in the normal group, $p<0.001$

22/23 in the emphysema group vs. 1/3 in the α-1 antitrypsin group, $p=0.027$

0/8 in the normal group vs. 1/3 in the α -1 antitrypsin group, $p=0.273$ p-value is based on Fisher's exact test

USE OF METALLOPROTEINASE INHIBITORS IN THE TREATMENT AND PREVENTION OF PULMONARY EMPHYSEMA

This application is a 371 of PCT/US98/10265 filed May 20, 1998 which filed claims the benefit of U.S. Provisional application No. 60/047,178, filed May 20, 1997, the contents of which are hereby incorporated by reference.

BACKGROUND OF THE INVENTION

Pulmonary emphysema, the major component leading to morbidity and mortality in chronic obstructive pulmonary disease (COPD), is the fourth leading cause of death in the United States. Approximately 15 million Americans are affected by COPD with an increasing incidence in women. Smoking is the major risk factor for COPD and accounts for over 90% of cases seen worldwide. Despite this finding, the standard treatment for COPD has changed little over the past 20–30 years.

The etiology of emphysema is multiplex with a variety of different injuries leading to the disease, including structural damage to the lung, defective proteinase inhibitors and diseases which result in overproduction of neutrophils within the lung (Aaron, 1983). Currently the major hypothesis for the pathogenesis of emphysema is the protease-antiprotease theory (Janoff, 1985). This states that an imbalance between the levels of degradative enzymes and their respective inhibitors damages the connective tissue matrix components of the lung.

Emphysema is estimated to affect 1.6 million Americans and has been shown to be directly related to cigarette smoking. Although the primary mechanism leading to lung destruction in this disease is believed to be secondary to an imbalance between proteases and antiproteases, direct evidence of an increase in destructive enzymes within the lung parenchyma has never been demonstrated. The hypothesis was based mainly on the induction of emphysema in animals through intratracheal instillation of nonspecific proteolytic enzymes (Gross et al., 1965). However, the major-focus of many studies has concentrated on elastase as the primary destructive protease due to two particular observations. First, the association between the absence of alpha-1 antitrypsin (an inhibitor of elastase) and emphysema was made through the characterization of the rare hereditary disease, alpha-1 antitrypsin deficiency (Laurell and Erikson, 1963). Secondly, pancreatic and leukocyte elastase produce an emphysema-like phenotype experimentally when instilled intratracheally into certain animal species (Janoff et al., 1977). By contrast, when bacterial collagenase was injected into the lungs of hamsters, no emphysematous lesions developed (Johansen and Pierce, 1972).

The degradation of elastin readily explains the early development of the disease in alpha-1 antitrypsin deficiency (Laurell and Erikson, 1963). However, this represents only 1% of all human patients who suffer from emphysema and the relationship of alpha-1 antitrypsin to the major form of human emphysema which is induced by cigarette smoking remains unclear. In fact, studies over the past 20 years have failed to demonstrate elastase excess or inhibitor deficiency in the development of other forms of human emphysema (for reviews, see Hance and Crystal, 1975). Even in alpha-1 antitrypsin deficiency human patients, there is no direct biochemical evidence for actual proteolysis of elastin in vivo (Hance and Crystal, 1975).

Most importantly perhaps, there are a number of discrepancies between the emphysema observed in the elastase-induced animal model and human emphysema. First, there are differences in the morphological phenotype which have been identified at the ultrastructural level. Secondly, the elastase-induced animals suffer from an acute severe hemorrhagic and inflammatory response which could induce a variety of nonspecific initiators of the emphysematous process (Hoidal et al., 1989). Thirdly, this acute form of emphysema induced after a single intratracheal instillation of enzyme is direct contrast to human emphysema which develops only after chronic insult to the tissue over a period of years. Overall, the lack of direct evidence has led a number of investigators to question the exact role of elastase in human emphysema (Hance and Crystal, 1975; Pickrell and Mauderly, 1981).

A major hypothesis for the pathogenesis of pulmonary emphysema is that alveolar destruction results from an imbalance between proteolytic enzymes and inhibitors in the lung parenchyma. However, direct evidence of an increase in destructive enzymes within the lung parenchyma is lacking.

Chronic obstructive pulmonary disease (COPD), consisting of emphysema and chronic bronchitis, is the fourth leading cause of death in the United States. Approximately 15 million Americans are affected by COPD and there is an increasing incidence in women. Smoking is the major risk factor for COPD and accounts for over 90% of cases seen worldwide. Despite this finding, there are no specific therapies available to limit or prevent these slowly progressive destructive changes (Snider).

Studies over the past 20 years have failed to demonstrate elastase excess or inhibitor deficiency in the development of human emphysema (for reviews, see Hance and Crystal, 1975,). Investigators have identified a variety of protease activity in the bronchoalveolar lavage of smokers. However, cigarette smoking is associated with a 5–10 fold increase in cells recovered by lavage and may not represent what is actually occurring within the lung parenchyma. The chronicity of emphysema and absence of smoking late in the disease make it difficult to implicate these enzymes in the progression of the disease process. This lack of direct evidence has led a number of investigators to question the exact role of elastase in human emphysema (Hance and Crystal, 1975; Pickrell and Mauderly, 1981).

We have previously demonstrated that chronic expression of human collagenase in transgenic mice causes emphysema (D'Armiento et al., 1992). The enzyme used in the animal studies is identical, immunologically and functionally, to the human collagenase of fibroblasts and macrohpages. Most significantly, both of these cell types have been shown to be present within the normal alveolar structure. The development of emphysema upon degradation of collagen in animals implicates this enzyme in the human disease. Despite the lack of evidence demonstrating elastase activity in patients with emphysema and the establishment of emphysema in transgenic mice with the over expression of collagenase (MMP-1), investigators have continued to focus on the role of elastolytic enzymes in the human disease (Shapiro, The pathogenesis of emphysema 30 years later). Most recently, researchers have identified a protease (metalloelastase) secreted by macrophages which is capable of degrading elastin and have hypothesized that this enzyme is responsible for human emphysema. The present study was therefore performed to determine if there was increased expression of collagenase or elastase in the lungs of human patients with emphysema as compared to normal controls.

Matrix metalloproteinase inhibitors are known to block the action of a family of enzymes, the matrix metalloproteinases (Brown, P. *Advan. Enzyme Requl.,* Vol 35, pp 293–300 1995). In the earliest experiments in animal cancer models, matrix metalloproteinase inhibitors were shown to block the spread of cancer and as a result were regarded initially as anti-metastic agents. Further, a series of experiments have shown that, in addition to blocking cancer spread, these inhibitors can also block cancer growth. Experiments have demonstrated this activity for a synthetic matrix metalloproteinase inhibitor, batimastat BB94 ("Batimastat")

The batimastat-collagenase complex is described in detail and the activities of batimastat analogues are discussed in the light of the protein-inhibitor interactions in Grams, F. *Biochemistry* 1995, 34. 14012–14020.

Synthesis of Batimastat (BB94) is described in Campion et al. (1990).

Other known metalloproteinase inhibitors include tetracycline and its derivatives including minocycline, and dilantin.

SUMMARY OF THE INVENTION

The subject invention provides a use of a metalloproteinase inhibitor for the preparation of a pharmaceutical composition for treating human pulmonary emphysema which comprises admixing the metalloproteinase inhibitor in an amount effective to treat human pulmonary emphysema and a pharmaceutically acceptable carrier.

The subject invention also provides A pharmaceutical composition which comprises a metalloproteinase inhibitor in an amount effective to to treat human pulmonary emphysema and a pharmaceutically acceptable carrier.

The subject invention provides a method for treating human pulmonary emphysema comprising administering a metalloproteinase inhibitor. The subject invention also provides a method for preventing human pulmonary emphysema comprising administering a metalloproteinase inhibitor.

The subject invention further provides the above-described methods wherein the metalloproteinase inhibitor is active against collagenase The subject invention also provides a method of treating mammals afflicted with a condition associated with the presence of collagenase in the lung tissue, comprising the step of administering to the individual a therapeutically effective amount of a metalloproteinase inhibitor of the present invention in a pharmaceutically acceptable composition.

The subject invention also provides a method of treating a subject in need of such treatment comprising administering by inhalation a metalloproteinase inhibitor active against collagenase in an amount effective to treat emphysema.

We previously demonstrated that chronic expression of human collagenase in the parenchyma of transgenic mice causes emphysema (D'Armiento et al., 1992). The pathology seen in the transgenic mouse lungs is strikingly similar to the morphological changes observed in human emphysema. The enzyme expressed in the animal studies is identical, immunologically and functionally, to the human collagenase of fibroblasts and macrophages. Both of these cell types are present within the normal alveolar structure. These findings led us to hypothesize that collagenase overexpression in the parenchyma of the lungs of patients with emphysema may contribute to the development and progression of the disease. To test this hypothesis, the present study was performed to determine the level of expression of collagenase and elastase in the lungs of patients with emphysema as compared to controls.

Recently, a transgenic mouse was generated which overexpressed the human enzyme collagenase (MMP-1) in the lung and the animals developed emphysema. We therefore hypothesized that an increase in this enzyme in human lungs may lead to emphysema.

Although emphysema is believed to be due to an imbalance in protease activity within the lung, a molecular analysis of the lung paranchyma from patients with emphysema has never been undertaken. This is the first direct demonstration at the RNA and protein level of a degradative enzyme in human emphysema tissue. This study shows that collagenase expression is present in patients with human emphysema secondary to cigarette smoking and not in normal patients or in alpha-1 antitrypsin deficiency patients who have not smoked. In addition, this study demonstrates that elastase expression and activity is not present in the lungs of patients with smoking induced emphysema.

Emphysema tissue obtained from lung reduction surgery was examined for the presence of collagenase (MMP-1), gelatinase (MMP-9), neutrophil elastase and metalloelastase mRNA through reverse transcriptase-PCR (RT-PCR) and ribonuclease protection assays and compared with normal lung tissue. Samples were obtained from 23 emphysema patients, 3 patients with alpha 1 antitrypsin deficiency and 8 control patients ranging from 39–60, 39–46 and 19–55 years in age, respectively. The samples were also examined for the presence of collagenase and elastase enzyme activity.

Collagenase mRNA was identified in 22 of the 23 emphysema patients, 1 out of 3 alpha-1 antitrypsin patients and 0 out of 8 control patients samples. Six out of seven samples tested from emphysema patients demonstrated collagenase protein by ELISA analysis with none of the controls demonstrating protein or enzyme activity. Elastase activity was found in only one samples which was from a patient with alpha 1 antitrypsin deficiency.

Although investigators have assayed the BAL fluid in emphysema patients for the presence of degradative enzymes, the lung paranchyma has never been examined. This is the first direct demonstration at the RNA and protein level of a degradative enzyme in smoking induced human emphysema tissue. The present data strongly suggest that collagenase-1 and not elastase, is a critical enzyme involved in the pathogenesis of human emphysema. The observation of increased collagenase (MMP-1) expression in the lung presents for the first time the possibility that inhibition of this enzyme would be feasible in the treatment and prevention of this human lung disease. The observation of increased collagenase (MMP-1) expression in the lung of patients with emphysema presents the possibility that this enzyme could be a target in the treatment and prevention of disease.

This study reports the first demonstration, at the RNA and protein level, of a degradative enzyme in human emphysema tissue. These data demonstrate that collagenase (MMP-1) is expressed in patients with emphysema secondary to cigarette smoking and is absent in normal patients. In contrast, neutrophil elastase expression and activity could not be detected in the lungs of patients with smoking induced emphysema and normal controls.

It is well established that only about 15% of long-term smokers will develop emphysema, whereas many patients with emphysema will experience progressive airflow obstruction even after they have stopped smoking. Animal studies have demonstrated that exposure to cigarette smoke increases collagenase expression and collagen degradation in the lung (Pardo, Wright). Immunohistochemical studies demonstrate that the collagenase expression is present in the macrophages, alveolar lining cells and interstitium. Therefore, it is conceivable that in humans the lung parenchyma is modified during the time period of smoking such that the collagenase enzyme is expressed. The present study demonstrate that even after smoking has ceased in the emphysema patients the collagenase continues to be expressed. The reasons for continued collagenase expression after smoking cessation are presently unknown. Our findings suggest that this collagenase expression plays a role in the continued progression of emphysema after smoking cessation. In addition, it is therefore possible that the fibroblasts in certain patients who are predisposed to emphysema have a greater potential to secrete the collagenase when exposed to cigarette smoke.

The present data strongly suggest that collagenase-1 is a critical enzyme involved in the pathogenesis of smoking induced human emphysema even after smoking has ceased. The combination of this study and the demonstration of lung destruction in transgenic animals through the overexpression of collagenase (MMP-1) leads one to hypothesize that the inhibition of this enzyme may be a suitable target to slow or arrest the progression of emphysema. Controlled trials of metalloproteinase inhibitors in emphysema can further support this hypothesis and provide a novel therapeutic intervention in the treatment of emphysema.

BRIEF DESCRIPTION OF THE FIGURES

FIG. 6. Clinical Characteristics of Patients Prior to Surgery

FIG. 7. Presence of Collagenase-1 Protein in Patients With Emphysema by ELISA

FIG. 8. Summary of Collagenase Expression

DETAILED DESCRIPTION OF THE INVENTION

Figure 1A:
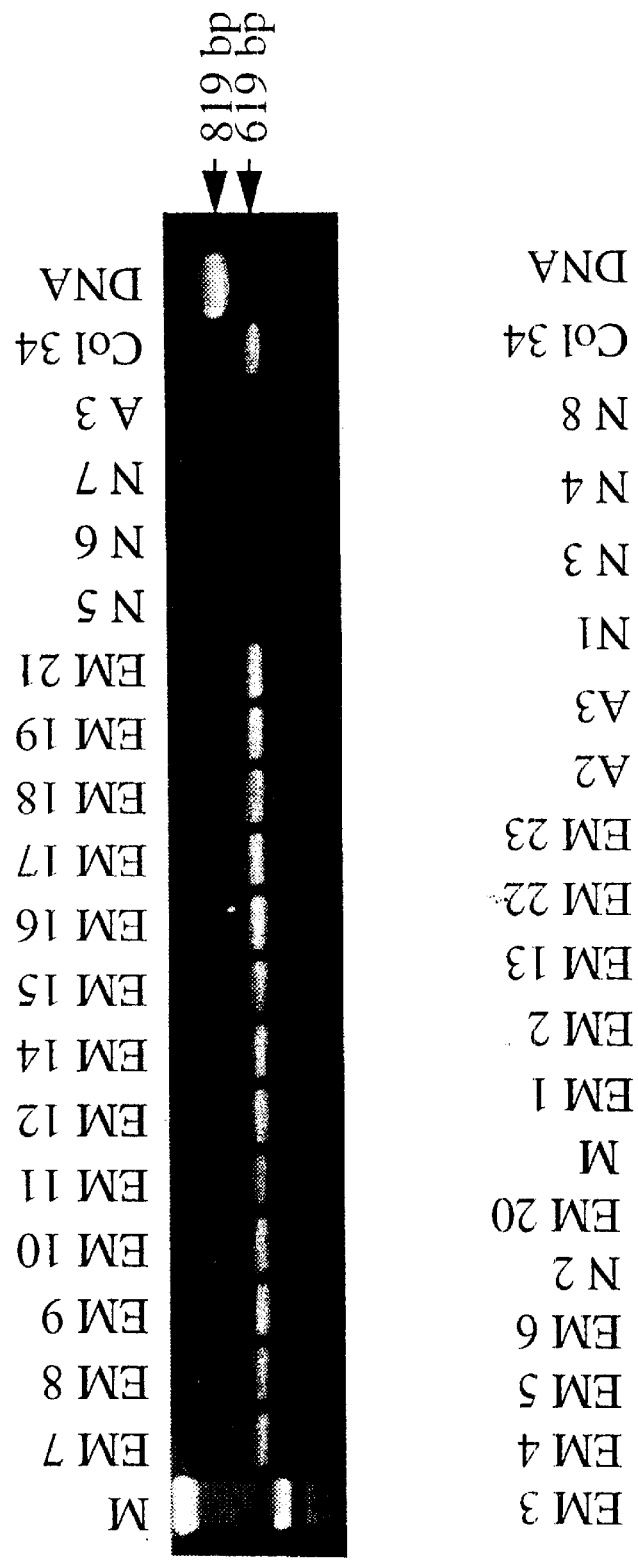
FIG. 1. Analysis of Collagenase (MMP-1) mRNA Expression in Human Lung Tissue.

The subject invention provides a use of a metalloproteinase inhibitor for the preparation of a pharmaceutical composition for treating human pulmonary emphysema which comprises admixing the metalloproteinase inhibitor in an amount effective to treat human pulmonary emphysema and a pharmaceutically acceptable carrier.

In another embodiment the invention provides a use of a metalloproteinase inhibitor wherein the metalloproteinase inhibitor is active against collagenase.

In a further embodiment the subject invention provides a use of a metalloproteinase inhibitor wherein the metalloproteinase inhibitor comprises batimastat, dilantin, tetracycline or minocycline.

In a further embodiment the subject invention provides a use of a metalloproteinase inhibitor wherein the effective amount is an amount corresponding to about 25 mg/kg of body mass to about 50 mg/kg of body mass or an amount corresponding to a blood plasma level of about 10 ng/ml to a blood plasma level of about 1000 ng/ml.

In a further embodiment the subject invention provides a use of a metalloproteinase inhibitor wherein the carrier is adapted for inhalation therapy.

The subject invention also provides a pharmaceutical composition which comprises a metalloproteinase inhibitor in an amount effective to treat human pulmonary emphysema and a pharmaceutically acceptable carrier.

In a another embodiment the subject invention provides a pharmaceutical composition wherein the metalloproteinase inhibitor is active against collagenase.

In a further embodiment the subject invention provides a pharmaceutical composition wherein the metalloproteinase inhibitor comprises batimastat, dilantin, tetracycline, or minocycline.

In a further embodiment the subject invention provides a pharmaceutical composition wherein the effective amount is an amount corresponding to about 25 mg/kg of body mass to about 50 mg/kg of body mass or a blood plasma level of about 100 ng/ml to a blood plasma level of about 1000 ng/ml.

In a further embodiment the subject invention provides a pharmaceutical composition wherein the carries is adapted for inhalation therapy.

The subject invention provides a method for treating human pulmonary emphysema comprising administering a metalloproteinase inhibitor.

The invention further provides a method for treating human pulmonary emphysema comprising administering an inhibitor that is active against collagenase.

The subject invention also provides a method of preventing human pulmonary emphysema comprising administering a metalloproteinase inhibitor.

The subject invention provides a method of treating mammals afflicted with a condition associated with the presence of collagenase in the lung tissue, including the condition of emphysema, comprising the step of administering to the individual a therapeutically effective amount of a metalloproteinase inhibitor of the present invention in a pharmaceutically acceptable composition.

According to the present invention, the treatment method may comprise inhalation of the composition.

The subject invention provides a method of treating a subject in need of such treatment comprising administering a metalloproteinase inhibitor active against collagenase in an amount effective to treat emphysema.

The invention further provides a method of treating a subject in need of such treatment comprising administering a metalloproteinase inhibitor active against collagenase in an amount effective to prevent emphysema.

The invention also provides a method of treating a subject in need of such treatment comprising administering by inhalation a metalloproteinase inhibitor active against collagenase in an amount effective to treat emphysema.

A total of 34 patients were enrolled for this study; 23 were emphysema patients, 8 normal patients, and 3 were alpha-1 antitrypsin patients. When analyzed by RT-PCR and RNAse protection assays, collagenase expression was detected in 22/23 (96%) of the emphysema patients and none of normal patients. This difference in rates was significant (p<0.001). The rate of collagenase expression was also statistically significant (p=0.027) for the patients in the emphysema group (22/23, 96%) when compared to the patients in the α-1 antitrypsin group (1/3, 33%). No significant difference in collagenase expression was observed between normal and the α-1 antitrypsin group (Table 3).

Collagenase is not only increased at the endstage of emphysema as is seen in most of the patients but also in clinically unapparent emphysema as was demonstrated with patients EM 2 and EM 18. These patients were 39 and 35 years of age, respectively without clinical signs of emphysema however, with a long history of smoking. When analyzed pathologically the lung from these patients demonstrated emphysematous changes and the levels of collagenase were increased at the RNA. The collagenase expression is also not as a result of the structural changes seen in emphysema since the patients with alpha 1 antitrypsin deficiency did not demonstrate increased collagenase within the lung. The patients analyzed with alpha-1 antitrypsin deficiency had emphysema at a clinically comparative level as the smoking induced emphysema patients as exemplified by the comparative $FEV_1/FVC$ ratios seen in each group.

The increase in collagenase mRNA is not secondary to the lung reduction procedure for two reasons. Collagenase was not shown to be increased in the lungs of alpha 1 antitrypsin patients undergoing lung reduction and two of the samples (EM 2 and EM 18) were collected from accident victims with long smoking histories and clinically unapparent emphysema. Since the collagenase enzyme is present in inflammatory cells including macrophages the possibility that the increase in the enzyme may be secondary to an inflammatory response in the tissue has been raised. This is not likely for several reasons. All specimens were examined histologically for any signs of infection and if present the sample was deleted from the study. Second, if the collagenase was increased secondary to inflammation, then other enzymes present in these inflammatory cells should have also been increased (such as metalloelastase and gelatinase b). Finally, the insitu hybridization studies demonstrate that collagenase mRNA is present in the lung fibroblasts.

Figure 4A:
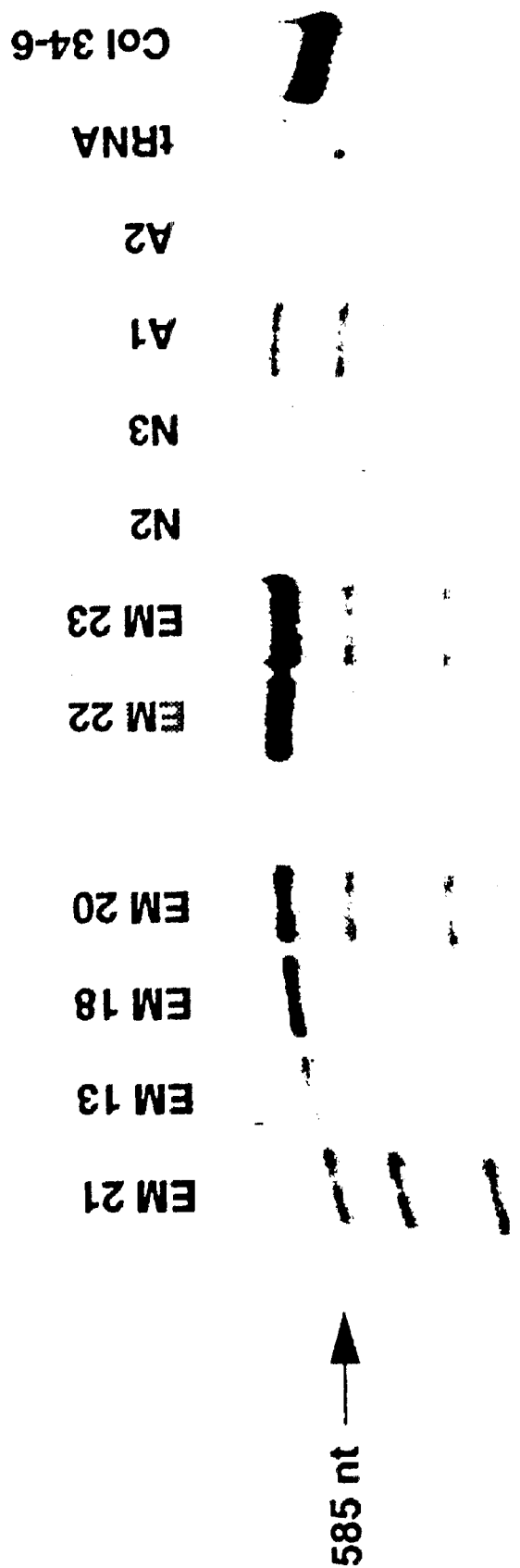
FIG. 4. RNAse Protection Analyses of Collagenase-1 and Neutrophil Elastase Expression in Human Lung Tissue.

The present study allows us to hypothesize as to what is occurring in the emphysematous lung during and after smoking. It is established that patients who develop emphysema continue to drop their $FEV_1/FVC$ ratio even after they have stopped smoking. Therefore, it is conceivable that the lung fibroblasts are modified during the time period of smoking such that the collagenase enzyme is expressed. This has been demonstrated to occur in hamsters when exposed to cigarette smoke (Pardo, AM J. Physiology). After patients have ceased smoking a percentage of individuals may continue to express the enzyme within their lung fibroblasts. Therefore, even though they are no longer exposed to cigarette smoke and the macrophage population in the lung diminishes, the fibroblasts continue to secrete the enzyme such that chronic destruction continues to occur. In addition, it is therefore probable that the fibroblasts in certain patients who are predisposed to emphysema have a greater potential to secrete the enzyme when exposed to cigarette smoke. One patient in our study (EM 23) developed emphysema at the age of 30 and does not have alpha 1 antitrypsin deficiency. The sample from this patient has a significant elevation in the mRNA for collagenase when compared to other samples (FIG. 4a). The sample from this patient can be examined more closely for the presence of factors which can upregulate collagenase.

Emphysema does not develop in all patients who have smoked. As alpha-1 antitrypsin deficiency has been found to increase the likelihood of emphysema in a select group of patients it is possible that alterations in the expression of collagenase or inhibitors of this enzyme may result in another subset of patients genetically predisposed to developing this lung disease.

Combined with the previous animal studies, the present data strongly suggest that collagenase-1, and not elastase or metalloelastase, is a critical enzyme involved in the pathogenesis of smoking induced human emphysema. From these studies it is not possible to definitively identify collagenase (MMP-1) as a cause of emphysema but certainly, the combination of the present study and the demonstration of lung destruction in transgenic animals through the overexpression of MMP-1 leads one to hypothesize that the inhibition of this enzyme may prevent the progression of emphysema. Controlled trials of metalloproteinase inhibitors in this lung disease can address this hypothesis and provide a novel therapeutic intervention in the treatment of emphysema.

Figure 1B:
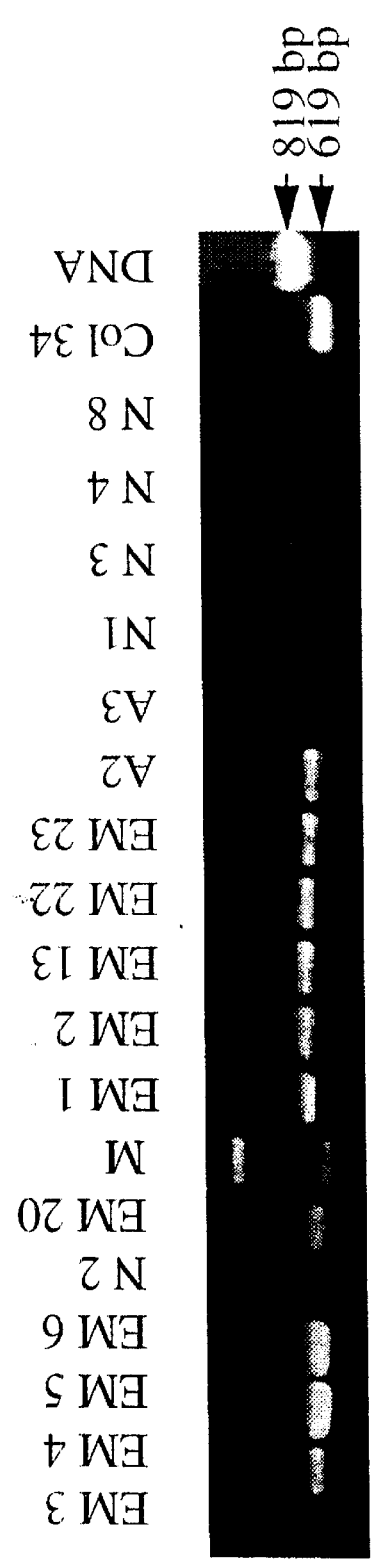

Referencing FIG. 1, total RNA was isolated from lung tissue of normal individuals and patients with emphysema. One microgram of RNA was used for reverse-transcription-PCR using primers designed from exons 9 and 10 of the collagenase-1 gene. The expected size of 619 bp was detected in 22/23 patients with emphysema (EM 1–23). Collagenase-1 expression was not detected in the 8 normal patients (N1–N8). In addition, one out of three patients with α-1-antitrypsin deficiency had collagenase-1 expression (A2–A3, A1 not shown). The DNA control shows the expected size of 819 bp. Col 34 is one microgram of total RNA from the lung of a transgenic mouse expressing human collagenase-1 (D'Armiento et al., 1992). M: 1 kb molecular weight marker (GIBCO-BRL)

Figure 2A:
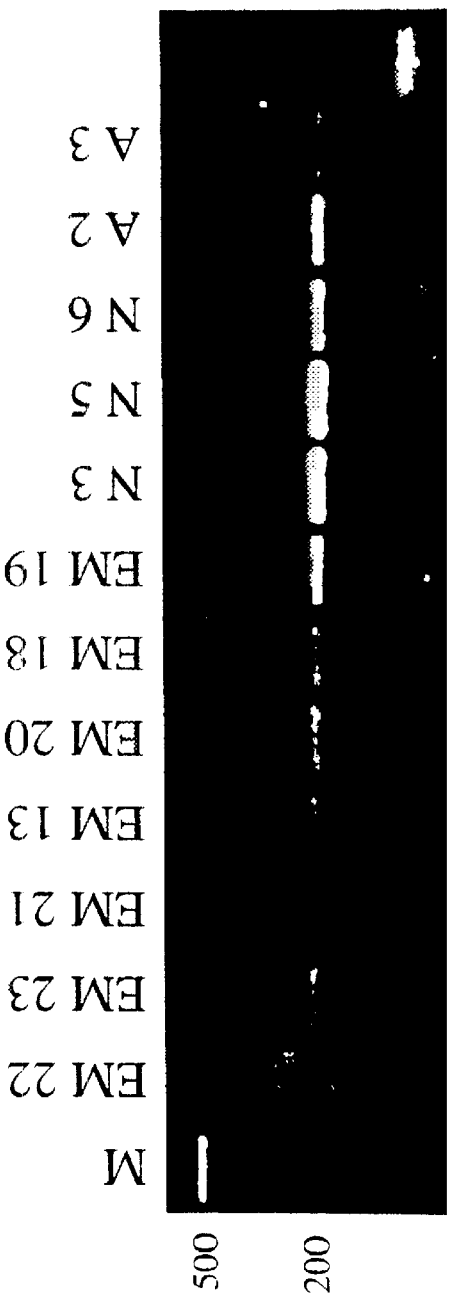
FIG. 2. Analysis of Elastase mRNA Expression in Human Lung Tissue
Figure 2B:
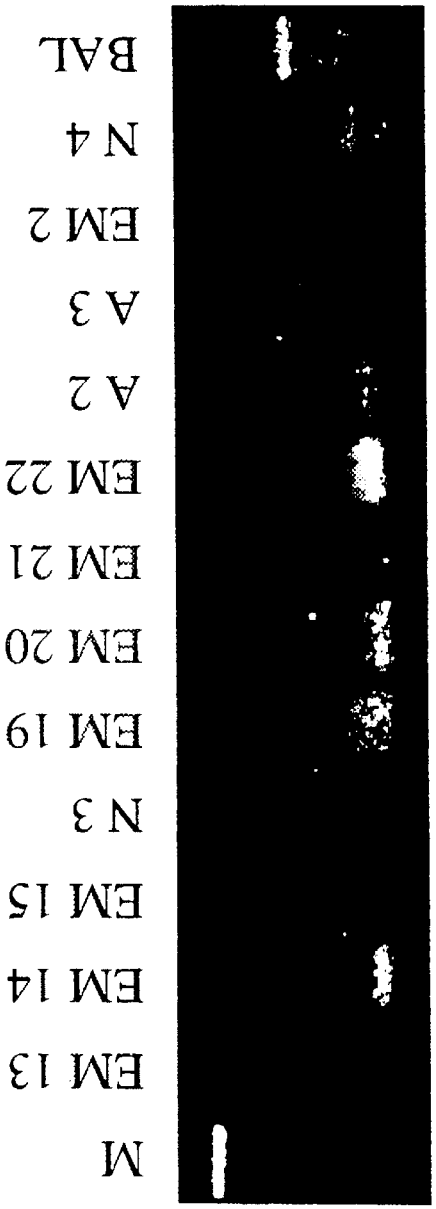

FIG. 2 Shows the Following a) Gelatinase-B expression in lungs of normal and emphysema patients.

Reverse transcription-PCR was performed using primers from exons 9 and 10 of the human gelatinase B gene. The expected size of 200 bp was present in all samples analyzed. For a negative control (–), one microgram of total RNA was used from a wildtype mouse. M: 1 kb ladder (GIBCO-BRL).

b) Lack of metalloelastase expression in patients with emphysema.

Reverse transcription-PCR was performed using primers from exons 9 and 10 of the human metalloelastase gene. The expected size of 200 bp was not present in any of the emphysema lungs nor the normal samples. For a positive control, one microgram of total RNA was used from macrophages isolated from the bronchiolavage of a patient (BAL).M: 1 kb ladder (GIBCO-BRL).

This is not the first demonstration of gelatinase b and Timp 1 expression in normal lung tissue, however the exact role of these proteins in lung function is not yet clear (Tokuraku). From the present studies, there is no correlation with expression of either gelatinase b or Timp 1 with emphysema.

In addition, reverse transcription-PCR was performed using primers from exons 2 and 3 of the human neutrophil elastase gene. The expected size of 259 bp was not present in any of the emphysema lungs nor the normal samples. For a positive control, one microgram of total RNA was used from human myelocytic cell line (HL-60).M: 1 kb ladder (GIBCO-BRL).

Figures 3A, 3B, 3C:
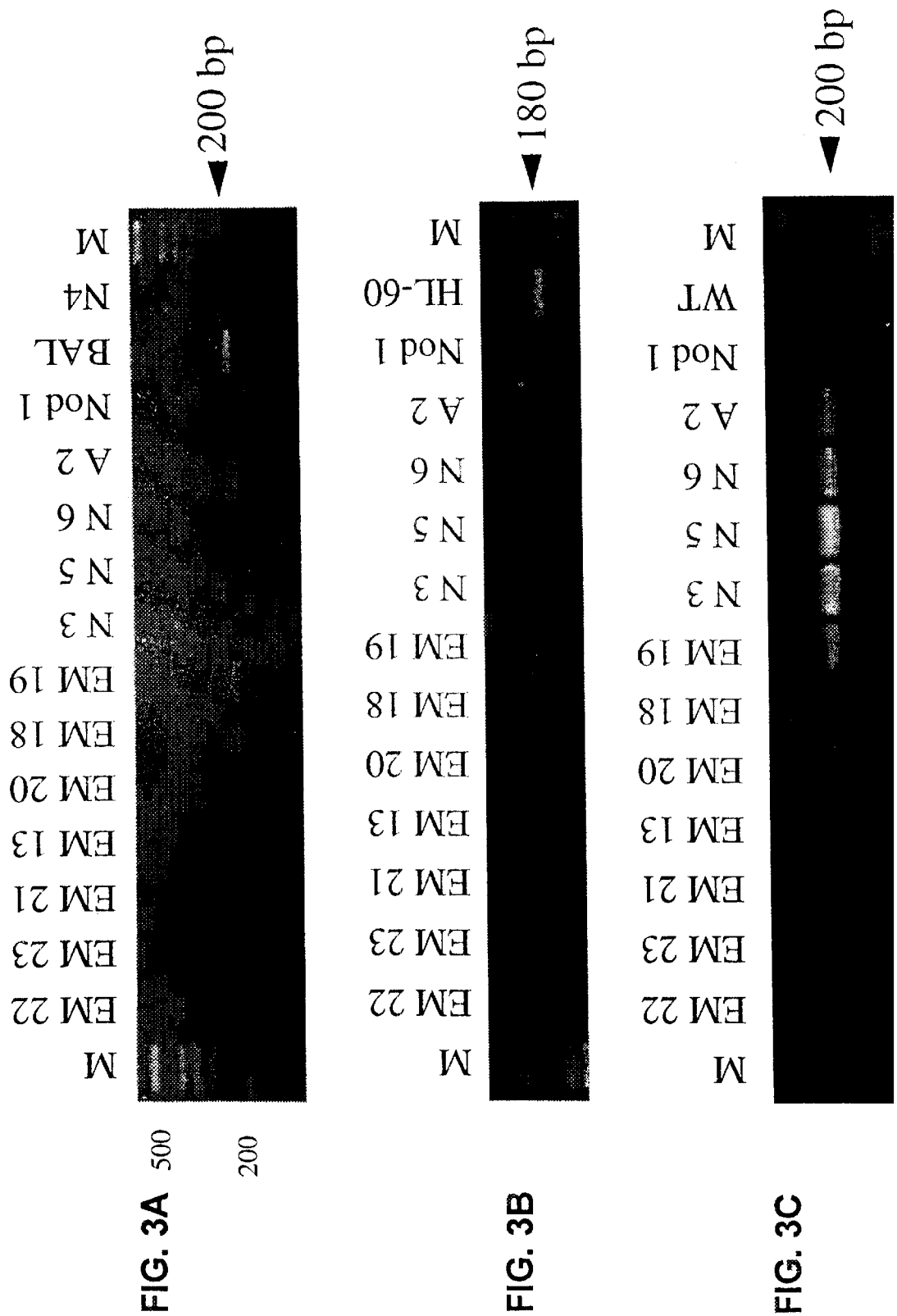
FIG. 3. Analyses of Protease mRNA Expression in Human Lung Tissue.
  a) Lack of metalloelastase expression in patients with emphysema.
  b) Neutrophil elastase expression in patients with emphysema.
  c) Gelatinase-B expression in lungs of normal and emphysema patients.

Referencing FIG. 3a, reverse transcription-PCR was performed using primers from exons 9 and 10 of the human metalloelastase gene. The expected size of 200 bp was present in the lung of only one emphysema sample (EM 19) and not any of the normal lung samples. Representative samples are shown in the figure. For a positive control, one microgram of total RNA was used from macrophages isolated from the broncheolavage of a patient (BAL). M: 1 kb molecular weight marker (GIBCO-BRL).

Referencing FIG. 3b, reverse transcription-PCR was performed using primers from exons 2 and 3 of the human neutrophil elastase gene. The expected size of 180 bp was not present in any of the samples tested. Representative samples are shown in the figure. For a positive control, one microgram of total RNA was used from a human myelocytic cell line (HL-60). M: 1 kb molecular weight marker (GIBCO-BRL).

Referencing 3c, reverse transcription-PCR was performed using primers from exons 9 and 10 of the human gelatinase B gene. The expected size of 200 bp was present in all samples analyzed. For a negative control (WT), one microgram of total RNA was used from macrophages isolated from a wildtype mouse. M: 1 kb molecular weight marker (GIBCO-BRL).

FIG. 4 Details the Following a) Collagenase-1 expression in lungs of patients with emphysema by RNAse protection analyses.

An 842 nucleotide (nt) radiolabeled antisense riboprobe was generated by in vitro transcription. The expected fragment size of 585 nt indicating collagenase-1 expression was found in patients with emphysema and in one patient with α1 antitrypsin deficiency. Collagenase-1 expression was not detected in the lungs of normal individuals. tRNA: yeast tRNA-negative control. Col 34-Total RNA from the lung of transgenic mouse expressing human collagenase-1 (D'Armiento et al., 1992).

b) Lack of neutrophil elastase (NE) expression in patients with emphysema. A 900 nt antisense riboprobe was generated by in vitro transcription. The expected fragment size of 159 nt indicating NE expression was not detected in any of the human lung samples. HL 60: one microgram of total RNA from a human myelocytic cell line. tRNA: yeast yRNA-negative control.

Figure 5:
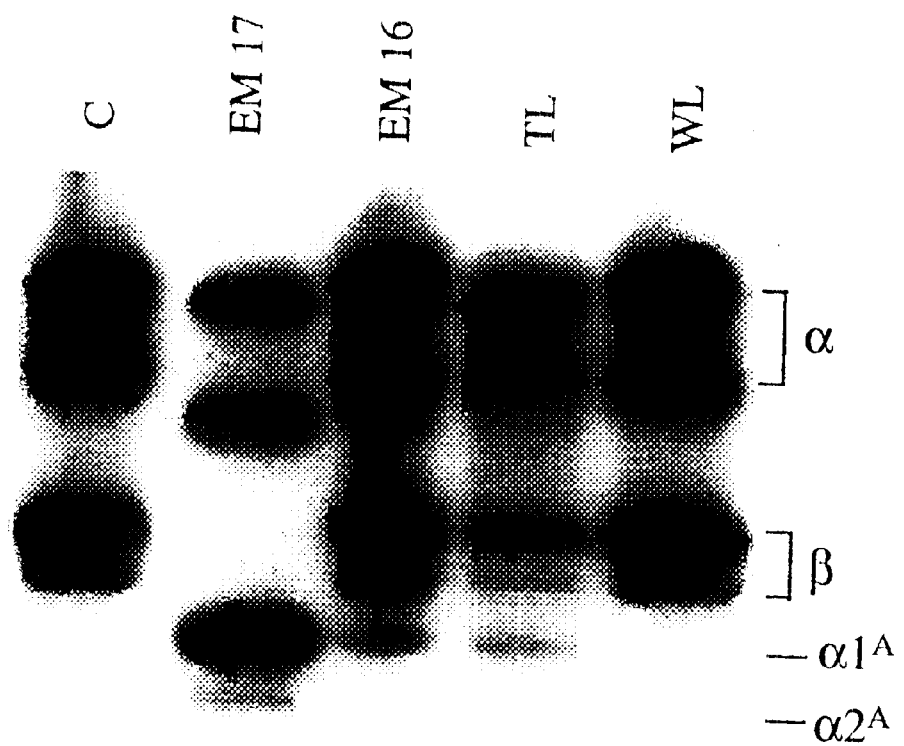
FIG. 5. Collagenase-1 Activity Detected in Patients With Emphysema Using a $^{125}$I-collagen Fibrillar Assay.

Referencing FIG. 5, type I$^{14}$C-collagen was incubated with buffer alone (C), 160 μg of protein homogenate from the lung of patient EM 17 and EM 16, 160 μg of protein homogenate from the lung of a transgenic mouse expressing collagenase in the lung (TL) and the lung homogenate from a wild type littermate (WL) (D'Armiento, 1992). The arrows indicate the characteristic α 1A, and α 2A fragments of the alpha chains of the type I collagen produced by interstitial collagenase. The digested products were analyzed by a 9% SDS-polyacrylamide gel.

Human lung samples were obtained from 1993–1996 at Columbia Presbyterian Medical Center (IRB# X042 1) from 27 patients with emphysema (Table I): 5 samples were obtained from recipient lungs during transplant; 20 samples were obtained during lung volume reduction procedures; two samples were obtained from lungs harvested for transplantation but rejected due to emphysematous changes. The major etiological factor for emphysema in these patients is cigarette smoking. (The clinical characteristics of the patients studied are listed in Table 1.) Normal tissue was obtained from 8 patients: Two were obtained from donor lungs harvested for transplant but not used due to recipient complications and a benign kidney mass; one was obtained from normal tissue after resection of a benign module, 5 were obtained from accidental death victims who were non-smokers.

Referencing Table 2, twenty micrograms of total human lung protein was used in a collagenase-1 ELISA assay (Amersham Life Science) to determine the levels of collagenase-1 protein. This assay is a 'sandwich' format in which polyclonal and monoclonal MMP-1 antibodies are used with a horseradish peroxidase detection method (see Methods). The lower limit of detection for the assay is 1 ng/ml. Collagenase-1 protein was detected in 4/5 patients with emphysema analyzed, and not detected in two normal samples, or the α-1-antitrypsin deficiency patient. (α-1-AT= alpha-1 antitrypsin deficiency)

The clinical characteristics of the 23 emphysema patients and the three α-1 antitrypsin deficiency patients are shown in Table 1. The mean age of the patients with emphysema was equal to 59+/−10.0 with 18 females (78%) and 5 males (22%). The normal patients range in age from 19–55 years with a mean of 32+/−13.9 with 3 females and 5 males. The FEV$_1$/FVC ratio in the patients ranged from 23%–52% predicted with the DLCO ranging from 7–92% of predicted values.

Expression of other degradative enzymes in this study show that metalloelastase is not consistently elevated either in patients with smoking-induced emphysema or α-1-antitrypsin deficiency. Absence of measurable elastase or metalloelastase does not exclude a pathogenic role for these enzymes, particularly early in the course of the disease.

Studies have shown that smoking leads to an acute increase in neutrophil elastase-derived fibrinopeptides in the serum of patients. Most, but not all, patients in our study had stopped smoking prior to surgery. Thus, it is probable that both elastase and collagenase contribute to the initial tissue damage during cigarette smoking while only collagenase contributes to disease progression after smoking has stopped. The enzymatic imbalance leading to emphysema involves a network of interrelated proteinases which contribute to the degradation of the connective tissue matrix components of the lung.

This study did not look specifically at patients with α-1-antitrypsin deficiency, but the few observations may be informative. Only one of three patients with α-1-antitrypsin deficiency expresses collagenase, and none expresses elastase. Elastase bioactivity, however, was present in the one patient tested. These data suggest that tissue destruction in patients with α-1 antitrypsin deficiency may not be mediated by either collagenase or elastase in the lung parenchyma. Elastase-like activity, as measured in the blood or bronchoalveolar lavage fluid, however, remains the leading mechanism for tissue destruction in patients with α-1-antitrypsin deficiency. Examination of tissue specimens in a larger group of patients with α-1-antitrypsin deficiency should clarify these tissues.

The collagenase expression seen in the emphysema patients is unlikely to be simply a consequence of the advanced structural changes observed in our patient population. Thus, two patients with α-1 antitrypsin deficiency did not demonstrate increased collagenase within the lung despite comparable degrees of airflow obstruction (Table 1). Furthermore, collagenase was not only increased in patients with advanced emphysema, but also in clinically unapparent emphysema as demonstrated in patients EM 2 and EM 18. These patients were 39 and 35 years of age, respectively, without clinical signs of emphysema. Each was a victim of trauma and a long history of smoking. Their lungs were deemed not to be suitable for transplantation based o the gross appearance of emphysema which was subsequently identified as centrilobular emphysema through pathological analysis.

Non-limiting examples of inhibitors of the present invention include the matrix metalloproteinase inhibitor batimastat (([(4-N-hydroxyamino)-2(R)-isobutyl-3(S)-(2-thienythiomethyl)succinyl]-L-phenylalanine-N-methylamide), ("batimastat"), dilantin, tetracycline and derivatives of tetracycline including minocycline.

Batimastat is a collagen peptide-based hydroxamic acid. Batimastat is classified as a broad spectrum matrix metalloproteinase inhibitor that mimics the site in the collagen substrate that is cleaved by the matrix metalloproteinase, collagenase. Modifications to this peptide structure have generated inhibitors with varying degrees of potency and specificity for members of the matrix metalloproteinase family. Batimastat's activity against a number of enzymes including collagenase has been documented. (Brown, supra.) (Reporting that batimastat is the first inhibitor of this class to enter clinical trial in cancer patients, and, in a phase I/II trial in patients with malignant ascites, batimastat was well tolerated and there were preliminary signs of efficacy.)

The metalloproteinase inhibitors of the present invention, including but not limited to batimastat, are administered in conjunction with a suitable pharmaceutical carrier. Representative examples of suitable carriers include, but are not limited to, mineral oil, alum, and synthetic polymers. Suitable pharmaceutical carriers are well known in the art and the selection of a suitable pharmaceutical carrier is deemed to be within the scope of those skilled in the art from the teachings contained herein. The selection of a suitable carrier is also dependent on the manner in which the metalloproteinase inhibitors are to be administered. The inhibitors may be administered orally, enterally, subcutaneously, intraperitoneally, intravenously, or intranasally. Preferred embodiments of the invention comprise oral, intraperitoneal, nasal administration and administration by inhalation. As used herein, "subject" may be an embryo, fetus, newborn, infant, or adult, Further, as used herein "treating" is contacting collagenase with the inhibitors of the present invention, alone or in combination with others compositions.

The present invention provides a method of treating mammals afflicted with a condition associated with the presence of collagenase in the lung tissue, which comprises the step of administering to the individual a therapeutically effective amount of a metalloproteinase inhibitor of the present invention in a pharmaceutically acceptable composition. Such composition may include a pharmaceutically acceptable carrier. Administration of the composition may be for either a prophylactic or therapeutic use. When provided prophylactically, the compositions provided in advance to the symptom caused by the condition afflicting the individual. When provided therapeutically, the composition is provided at, or shortly, after, the onset of any symptoms of the disease. The therapeutic administration of the composition serves to attenuate the condition. Examples of conditions and diseases which can be treated using a composition containing a novel processed substrate or substrates of the present invention include emphysema. Veterinary uses are also intended to be encompassed by this invention.

One embodiment of the present invention comprises administration of about 25 mg/kg to about 50 mg/kg per day of a metalloproteinase inhibitor. Another embodiment of the present invention comprises administration of a metalloproteinase inhibitor in an amount sufficient to maintain blood plasma levels of the inhibitor at 100 ng/ml–1000 ng/ml.

However, the amount of the composition containing the novel substrate(s) administered will vary upon the stage of progression of the disease or syndrome, the weight of the individual, and the efficacy of the composition containing the novel substrate(s). One of skill in the art will know the parameters to evaluate the response of the individual to the composition containing the novel substrate(s) and establish the dosage based on those parameters. Such therapies may be administered as often as necessary and for the period of time judged necessary by the treating physician.

Experimental Details

Methods Emphysema tissue was obtained from surgical specimens of 23 patients with emphysema, three patients with α-1-antitrypsin deficiency and eight control patients. The tissue was examined for the presence of collagenase (MMP-1), gelatinase (MMP-9), neutrophil elastase and metalloelastase mRNA through reverse transcriptase-PCR (RT-PCR) and ribonuclease protection assays and compared with normal lung tissue, and for the presence of collagenase and elastase enzyme activity.

Results Collagenase mRNA was identified in 22 of the 23 patients with emphysema, one of three α-1 antitrypsin patients and none of eight controls. In contrast, elastase expression was absent in all 23 patients with emphysema as well as all controls. The presence of collagenase protein was confirmed by demonstrating collagenase protein and activity in the emphysema lung samples. Elastase activity was present in only one sample from a patient with α-1 antitrypsin deficiency.

Patients

Lung tissue was obtained from twenty four patients with emphysema, 3 patients with alpha-1 antitrypsin deficiency, one patient with a benign nodular lung disease and 8 normal controls. The clinical characteristics of the 23 emphysema patients, the 3 alpha-1 antitrypsin deficiency patients and the one patient with benign nodular lung disease are all shown in table 1. The average age of the patients was equal to 59 with 18 females and 5 males. There were eight normal controls ranging in age from 19–55 years of age (Mean-29) with 3 females and 5 males. The $FEV_1/FVC$ ratio in the patients ranged from 23%–52% predicted with the DLCO ranging from 7–92.

Analysis of RNA from the Lung Tissue

After isolating total RNA from the lung, the samples were analyzed through RT-PCR for the presence of collagenase (MMP-1), neutrophil elastase, metalloelastase (MMP-12), gelatinase B (MMP-9) and tissue inhibitor of metalloproteinase-1 (TIMP-1). Only the collagenase mRNA was increased in the samples from patients with emphysema but not in RNA from the lungs of normal patients (FIG. 1A) The increase in collagenase expression was specific to the patients with smoking induced emphysema as exemplified through the analysis of three alpha 1 antitrypsin patients. Only one sample from the patient who was a long time smoker actually demonstrated a faint signal for collagenase (FIG. 1). Both neutrophil elastase and metalloelastase were not present in smoking induced emphysema and alpha-1 antitrypsin deficiency samples (FIGS. 3A, B). Gelatinase B (MMP-9) was found to be present in both the normal samples and the patients samples (FIG. 3C). The TIMP-1 RNA levels in the emphysema samples were variable and it appears that the TIMP-1 levels did not correlate with the emphysema phenotype.

The RT-PCR analysis is not quantitative and therefore when collagenase RNA was found to be present in the lung of patients with emphysema, an RNAse protection assay was performed to compare the level of expression between patients samples. Twenty two out of twenty three of the samples from the emphysema patients demonstrated a protected fragment specific for collagenase with none (0/8) of the normal samples expressing collagenase (Table 3, FIG.

4a). Also, when patients with alpha 1 antitrypsin were analyzed for expression of collagenase only the one patient with a long smoking history was shown to express collagenase and at a very low level (Table 3, FIG. 4a). The identical samples were then analyzed for the presence of neutrophil elastase RNA with all of the samples negative for neutrophil elastase RNA by RNAse protection assay (FIG. 4b).

All of the samples were analyzed by RT-PCR for the presence of collagenase (MMP-1), neutrophil elastase, metalloelastase (MMP-12), gelatinase B (MMP-9) and tissue inhibitor of metalloproteinase-1 (TIMP-1). Collagenase mRNA was detected in 22/23 (96%) of the tissue samples from patients with emphysema but not in the lung samples of normal patients (FIG. 1). Collagenase expression was present in one of three patients with α-1 antitrypsin deficiency (FIG. 1). In contrast to these findings, neutrophil elastase could not be detected in any of the lung samples. As a positive control the mRNA for neutrophil elastase was present in the HL-60 cell line. Metalloelastase was present in 1/23 samples from smoking induced emphysema and none of the α-1 antitrypsin deficiency samples. As a positive control mRNA was detected in the cultured macrophages from a bronchoalveolar lavage of a patient. Representative samples are shown in FIGS. 3A and B. Gelatinase B (MMP-9) is another metalloproteinase with a broad spectrum of substrate specificity including elastin. When the lung samples were analyzed for the presence of gelatinase B enzyme was present in all analyzed emphysema samples (22/22) and control samples (8/8). Representative samples are shown in FIG. 3C.

Since RT-PCR analysis is not quantitative, an RNAse protection assay was performed to compare the level of expression between patients samples. Twenty-two out of 23 of the samples from emphysema patients demonstrated a protected fragment specific for collagenase with none (0/8) of the normal samples expressing collagenase (data not shown). No correlation was found between severity of emphysema and collagenase mRNA levels. One of the major inhibitors of the collagenase enzyme is tissue inhibitor of metalloproteinase-1 (TIMP-1). Therefore, to examine whether levels of TIMP-1 mRNA were altered in emphysema the samples were examined by Northern blot analysis. TIMP-1 mRNA was found to be present in both normal and emphysema samples without a consistent correlation of levels with either group (data not shown).

Protein Assays

In order to correlate RNA expression with protein, we first performed an Elisa assay on the tissue homogenate from human lung samples and were able to detect protein in the emphysema samples and not in the normal sample (Table 2). We subsequently analyzed the homogenates for collagenase using rat tail type I collagen. The characteristic degradation pattern of mammalian collagenase was seen in samples from the patients with emphysema demonstrating not only the presence of protein but also enzyme activity. This was compared to the collagenase activity found in the tissue homogenate from a lung of a transgenic noise expressing collagenase (MMP-1) in the lung. We also analyzed the lung samples shown in Table 2 for the presence of elastase activity to confirm that there was indeed no elastase enzyme present in the tissue. Only one sample from patient A2 demonstrated elastase activity (data not shown). This sample is the same α-1-antitrypsin samples which demonstrated collagenase mRNA.

It is important to note that neutrophils carry very little RNA therefore we assayed the lung for the presence of elastase activity to confirm that there was indeed no enzyme present in the tissue. Only one sample from patient A2 demonstrated elastase activity. This is consistent with the alpha 1 antitrypsin deficiency phenotype which exhibits elastase activity in the blood. It is not possible to differentiate whether the elastase enzyme activity in this sample is from the lung or from the blood.

In situ Hybridization

In situ was then performed using digoxigenin labeled collagenase probe, as is shown in FIG. 4a.

In summary, a total of 34 patients were enrolled for this study; 23 were emphysema patients, 8 normal patients, and 3 were alpha-1 antitrypsin patients. When analyzed by RT-PCR and RNAse protection assay, collagenase expression was detected in 22/23 (96%) of the emphysema patients and none of the normal patients. This difference in rates was very highly significant (p<0.002). The rate of collagenase expression was also statistically significant (p=0.027) for the patients in the emphysema group (22/23, 96%) when compared to the patients in the alpha-1 antitrypsin group (1/3, 33%). No significant difference in collagenase expression was observed between normal and the alpha-1 antitrypsin group.

A 2 cm×2 cm piece of lung was analyzed immediately after removal from the patient. Ninety percent of the first 20 tissue samples was used from RNA isolation (EM1-EM15, EM17, EM18, EM21, N1, N2, N4–N8, A1, A3) while the remaining portion was examined histologically. Subsequently, for the remaining 8 samples (EM16, EM19 EM20, EM22, EM23, A2, LN 1, N3) five percent was placed in 4% formaldehyde for histology, twenty five percent was homogenized to prepare protein and 70% was used to isolate total RNA. Histological examination was conducted to exclude all samples with pathological evidence of inflammation or neoplastic changes from this study.

Isolation of Total RNA

Total RNA was prepared from fresh tissue using the guanidinium thiocyanate-cesium chloride method as previously described (Chirgwin et al., 1979). Tissue was homogenized with a polytron in a 4M guanidinium-thiocyanate solution. The homogenate was loaded onto a cesiumchloride cushion, and the samples were ultracentrifuged for 20 hours at 36,000 rpm. The RNA pellet was resuspended in a 7.5M guanidine-HCl solution, and precipitated with 1M acetic acid. The total RNA was finally resuspended in dimethyl pyrocarbonate-treated water and the absorbance was read at $A_{260}$ and $A_{280}$. The quality of the RNA was checked on a 1.2% denaturing agarose gel to ensure the presence of the 28S and 18S ribosomal bands.

Ribonuclease Protection Assay

Ribonuclease (RNAse) protection assays were performed as previously described (D'Armiento et al., 1995). Briefly, an 842 nucleotide antisense riboprobe was made in vitro using a portion of intron 9 and exon 10 of the human interstitial collagenase gene (MMP-1). Twenty micrograms of each total human lung RNA sample was hybridized overnight with excess $^{32}$P-labeled RNA probe at 45° C. in 40 mM PIPES (pH 6.4), 0.4M NaCl, 1 mM EDTA, and 80% formamide in a total volume of 30 $\mu$l. After hybridization, the samples were each treated with 20 units of RNAse T2 at 30° C. for 40 mins, followed by 50 $\mu$g of proteinase K for 15 mins at 37° C., phenol-chloroform extracted, and ethanol precipitated. Samples were analyzed on a 4% ureapolyacrylamide denaturing gel with a protected fragment of 585 nucleotides expected.

Reverse Transcription PCR (RT-PCR)

The primers were designed from exons 9 (AGC ACA TGA CTT TCC TGG AAT TGG C) and 10 (ATT TTG TGT TAG AAG AGT TAT CC) of the human collagenase-1 gene (MMP-1) (Goldberg et al., 1986). A PCR product of 819 bp is expected from genomic DNA and a product of 619 bp from RNA or cDNA. For the detection of the human metalloelastase mRNA (MMP-12), primers were also designed from exons 9 (ATG ATG AAA GGA GAC AGA TGA TGG) and 10 (ACA ACC AAA CCA GCT ATT GC) (Shapiro et al., 1993). A genomic PCR product of 1.2 kb and cDNA product of 200 bp is expected. For the detection of the gelatinase B mRNA (MMP-9), primes were designed from exons 9 (GGC AGG ACC GTC TCT ACT GGC GCG T) and 10 (CAG AAC AGA ATA CCA GTT TGT ATC) For the detection of the neutrophil elastase mRNA, primers were designed from exons 2 (CTG ATT GCG CCC AAC TTC GTC ATG T) and 3 (TAC GAC CCC GTA AAC TTG CTC AAC GA). The reverse transcription reaction was performed using 1 μg of total RNA, 300 ng/μl of primers, 200 units of Moloney-murine leukemia virus reverse transcriptase (M-MLV) from BRL, and 0.4 mM deoxyribonucleic acid nucleotides from Pharmacia in the presence of 1× first strand buffer (BRL: 0.50 M Tris-HCl, pH 8.3, 0.075 M KCl, 3 mM $MgCl_2$). The reaction was carried out at 37° C. for 1 hour. Two microliters of the reaction was then denatured for 5 minutes in a 50 μl reaction volume containing 0.4 mM of dNTPs, 300 ng/ml primers an d1 until Taq DNA polymerase (BRL) at 95° C. in the presence of 1X PCR buffer (BRL: 20 mM Tris-HCl, pH 8.4, 50 mM KCl, 2.5 mM $MgCl_2$). PCR amplification was performed using 30 cycles under the following conditions: 1 minute at 50° C., 1 minute at 72° C., and 1 minute at 94° C. in a thermal DNA cycler machine (Hybaid). Ten microliters of the reaction product was then analyzed on a 1.0% agarose gel.

Determination of Total Protein Concentration

Fresh human lung tissue was homogenized in TNC buffer (50 mM Tris-HCl, pH 7.5, 150 mM NaCl, 10 mM $CaCl_2$, 0.05% Brij, 0.02% $NaN_3$) using a polytron. The homogenate was centrifuged to sediment any particulate matter. The samples were concentrated using Centricon-30 columns (Amicon) to an approximate volume of 1–3 mls. The total protein concentration was determined using the standard BCA method (Pierce). For subsequent protein assays, equal amounts of total protein was used.

Human Collagenase-1 ELISA

The Biotrak™ human MMP-1 ELISA system was used from Amersham™. The assay is based on a two site ELISA 'sandwich' format. The standards and 400 micrograms total protein of each sample were incubated in wells precoated with 100 ng monoclonal anti-MMP-1 antibody for 2 hours at room temperature (15–30° C.). Wells were washed four times with PBS containing 0.05% Tween 20, and a second polyclonal MMP-1 antibody was added (200 ng of biotin-labelled rabbit anti-MMP-1) and incubated for 2 hours at room temperature. Wells were washed four times and incubated with horseradish peroxidase-linked streptavidin for one hour at room temperature. Wells were washed again four times and a solution of TMB substrate was added and incubated for 30 minutes at room temperature. The reaction was stopped with 100 μl of 1M sulfuric acid and the absorbance at 450 nm was measured.

Collagenase-1 Protein Assay

The lung homogenate in TNC buffer was treated with 1.5 mM p-aminophenylmercuric acetate (APMA) for 16 hours at 37° C. to activate latent collagenase. Twenty micrograms of each sample was incubated with type I $^4$C-collagen (rat tail) in a total volume of twenty microliters at 27° C. for 16 hours. The digestion products were analyzed by SDS-polyacrylamide gel electrophoresis (9%).

Statistics

Data was analyzed using SAS (Statistical Analysis System computer program for Microsoft Windows (Version 6.12). The data listings, descriptive statistics, and frequency distributions were generated using SAS programming. The rates for collagenase expression were compared using Fisher's exact test.

What is claimed is:

1. A method of treating human pulmonary emphysema in a subject in need of such treatment comprising administering to the subject an amount of a matrix metalloproteinase inhibitor effective to treat the human pulmonary emphysema and a pharmaceutically acceptable carrier, thereby treating the human pulmonary emphysema in the subject, wherein the matrix metalloproteinase inhibitor is a hydroxamic acid.

2. The method of claim 1, wherein the matrix metalloproteinase inhibitor is batimastat.

3. The method of claim 1, wherein the effective amount is an amount corresponding to about 25 mg/kg of body mass to about 50 mg/kg of body mass.

4. The method of claim 1, wherein the effective amount is an amount corresponding to a blood plasma level in the subject of about 100 ng/ml to about 1000 ng/ml.

5. The method of claim 1, wherein the carrier is adapted for inhalation therapy.

* * * * *